United States Patent [19]

Ertl

[11] Patent Number: 4,745,192
[45] Date of Patent: May 17, 1988

[54] 1-OXA-3-OXO-4,8-DIAZA-SPIRO(4,5)DECANE COMPOUNDS

[75] Inventor: Josef Ertl, Wertingen, Fed. Rep. of Germany

[73] Assignee: Hoechst Aktiengesellschaft, Frankfurt am Main, Fed. Rep. of Germany

[21] Appl. No.: 883,353

[22] Filed: Jul. 8, 1986

[30] Foreign Application Priority Data

Jul. 10, 1985 [DE] Fed. Rep. of Germany ....... 3524542

[51] Int. Cl.[4] .................... C07D 498/10; C08K 5/35
[52] U.S. Cl. ........................... 546/19; 524/94
[58] Field of Search .......................... 546/19

[56] References Cited

U.S. PATENT DOCUMENTS

| | | | |
|---|---|---|---|
| 4,314,933 | 2/1982 | Berner | 428/416 |
| 4,405,735 | 9/1983 | Wiezer et al. | 546/19 |

FOREIGN PATENT DOCUMENTS

| | | |
|---|---|---|
| 0095076 | 11/1983 | European Pat. Off. |
| 0094605 | 11/1983 | European Pat. Off. |
| 2063573 | 7/1972 | Fed. Rep. of Germany |
| 2738340 | 3/1979 | Fed. Rep. of Germany |
| 2933732 | 3/1981 | Fed. Rep. of Germany |
| 3149453 | 8/1982 | Fed. Rep. of Germany |
| 3217734 | 11/1983 | Fed. Rep. of Germany ........ 546/19 |
| 3408949 | 9/1984 | Fed. Rep. of Germany |

*Primary Examiner*—John Kight
*Assistant Examiner*—Kriellion Morgan

[57] ABSTRACT

1-Oxa-3-oxo-4,8-diaza-spiro[4,5]decane compounds of the formula

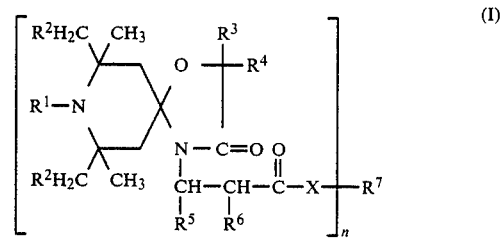

are novel light stabilizers for protecting polymers from the damaging effect of UV radiation.

2 Claims, No Drawings

1-OXA-3-OXO-4,8-DIAZA-SPIRO(4,5)DECANE COMPOUNDS

The invention relates to 1-oxa-3-oxo-4,8-diaza-sprio[4,5] decane compounds, which can be used as light stabilizers for polymers or as intermediates for the preparation of plastic additives, and to a process for their preparation.

Compounds of the formula

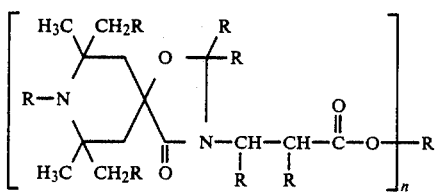

are known (cf. German Offenlegungsscuhrift No. 3,149,453). However, the process for their preparation is complicated, since the reaction medium is changed several times during the reaction, and this involves additional extractions and distillations.

Novel 1-oxa-3-oxo-4,8-diaza-spiro[4,5] decane compounds have now been found.

The invention thus relates to 1-oxa-3-oxo-4,8-diaza-spiro[4,5] decane compounds of the formula I, and to a process for their simplified preparation,

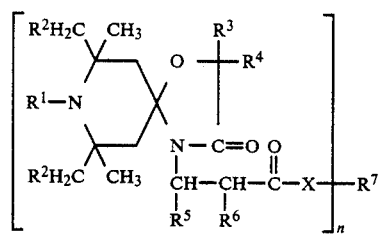

in which n is an integer from 1 to 4, $R^1$ is hydrogen, $C_1$–$C_4$-alkyl, benzyl, allyl, $C_2$–$C_{30}$-alkanoyl, $C_3$–$C_{20}$-alkenoyl, $C_7$–$C_{11}$-aroyl, $C_8$–$C_{14}$-arylalkanoyl or $C_8$–$C_{20}$-alkylaryl, $R^2$ is hydrogen or $C_1$–$C_4$-alkyl, $R^3$ is hydrogen, $C_1$–$C_{18}$-alkyl, $C_5$–$C_{12}$-cycloalkyl, a phenyl or naphthyl group which can be substituted by chlorine or $C_1$–$C_4$-alkyl, or a $C_7$–$C_{12}$-phenylalkylene group which may be unsubstituted or substituted by $C_1$–$C_4$-alkyl, $R^4$ is hydrogen, $C_1$–$C_4$-alkyl, $C_5$–$C_{12}$-cycloalkyl, $C_1$–$C_3$-alkenyl which is substitute by —COOH, carbo-$C_1$–$C_4$-alkoxy or carbamoyl, a phenyl, naphthyl or pyridyl group which can be substituted by $C_1$–$C_4$-alkoxy or $C_1$–$C_4$-alkyl, or a $C_7$–$C_{12}$-phenylalkyl group which can be substituted by $C_1$–$C_4$-alkyl, or $R^3$ and $R^4$, together with the carbon atom linking them, form a $C_5$–$C_{12}$-cycloalkyl group, which can be monosubstituted to tetrasubstituted by $C_1$–$C_4$-alkyl groups, or a radical of the formula II

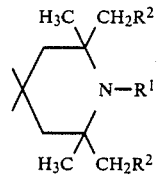

wherein $R^1$ and $R^2$ are as defined above, $R^5$ is hydrogen, methyl, phenyl or carbo-$C_1$–$C_{21}$-alkoxy, $R^6$ is hydrogen or methyl, $R^7$ is, if n=1, hydrogen, $C_1$–$C_{21}$-alkyl, $C_2$–$C_{22}$-alkenyl, $C_7$–$C_{18}$-phenylalkyl, $C_5$–$C_{12}$-cycloalkyl, phenyl, naphthyl, $C_7$–$C_{18}$-alkylphenyl, a radical of the formula

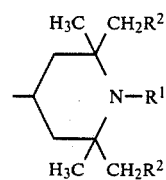

in which $R^1$ and $R^2$ are as defined above, or $C_2$–$C_{20}$-alkyl which can be interrupted by —O— or

and/or substituted by a radical of the formula III

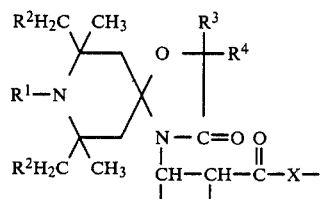

or by $C_1$'$C_{21}$-alkylcarboxyl, $R^1$, $R^2$, $R^3$, $R^4$, $R^5$ and $R^6$ being as defined above and $R^8$ being hydrogen, $C_1$–$C_{10}$-alkyl or a radical of the formula

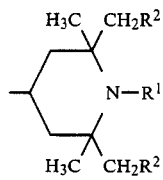

in which $R^1$ and $R^2$ are as defined above, or $R^7$ is, if n=2, a straight-chain or branch $C_1$–$C_{30}$-alkylene, $C_2$–$C_{30}$-alkenylene or phenyldialkylene, which radicals can be interrupted by —O— or

$R^8$ being as defined above, or $R^7$ is, if n=3 or 4, a radical of the formulae IV, V, VI or VII

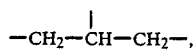
(IV)

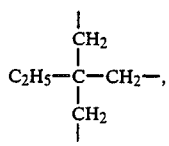
(V)

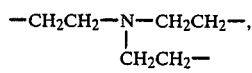
(VI)

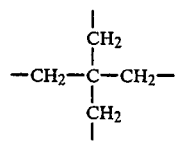
(VII)

and X is —O— or

$R^8$ being as defined above. Preferably, n is 1 or 2.

$R^1$ is preferably hydrogen, $C_1$-$C_4$-alkyl or $C_2$-$C_{18}$-alkanoyl, for example methyl, ethyl, propyl, butyl, acetyl, propionyl, butyryl, lauroyl or stearoyl, and particularly preferably hydrogen or one of the acid radicals mentioned. Especially, $R^1$ is hydrogen.

$R^2$ preferably is hydrogen or $C_1$-$C_4$-alkyl, for example methyl, ethyl, propyl or butyl. Especially, $R^2$ is hydrogen.

$R^3$ and $R^4$ independently of one another are $C_1$-$C_{18}$-alkyl, $C_5$-$C_{12}$-cyloalkyl or phenyl, for example ethyl, butyl, octyl, lauryl, stearyl, cyclohexyl or cyclodecyl, and particularly preferably $C_1$-$C_7$-alkyl. Especially, $R^3$ and $R^4$ are $C_1$-$C_4$-alkyl, for example methyl.

$R^3$ and $R^4$, together with the carbon linking them, are preferably $C_5$-$C_{12}$-cycloalkylene, particularly preferably $C_6$-or $C_{12}$-cycloalkylene, an especially cyclododecylene.

$R^5$ is preferably hydrogen, methyl or phenyl, and particularly preferably hydrogen.

$R^6$ is preferably hydrogen or methyl. Especially, $R^6$ is hydrogen.

$R^7$ is preferably $C_1$-$C_{21}$-alkyl or straight-chain or branch $C_1$-$C_{30}$-alkylene, for example methyl, butyl, octyl, lauryl, myristyl, stearyl, ethylidene, butylidene or hexylidene, and particularly preferably $C_1$-$C_{15}$-alkyl or $C_2$-$C_6$-alkylene. Especially, $R^7$ is $C_{12}$-$C_{14}$-alkyl, for example lauryl or $C_2$- or $C_6$-alkylene, for example hexylene.

$R^8$ is preferably hydrogen or 2,2,6,6-tetraalkylpiperid-4-yl, especially 2,2,6,6-tetramethylpiperid-4-yl.

The compounds of the formula I are formed by reacting compounds of the formula VIII

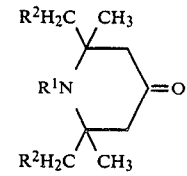
(VIII)

with compounds of the formula IX

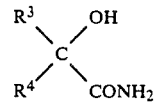
(IX)

n, $R^1$, $R^2$, $R^3$, $R^4$, $R^5$, $R^6$, $R^7$ and x being as defined above, in an inert solvent at a temperature of 30° to 150° C. in the presence of a basic catalyst, the reaction being carried out in the presence of 0.05 to 20 mol%, relative to compound VIII, of a phase transfer catalyst in an aromatic hydrocarbon which is liquid at room temperature.

The compounds of the formula VIII can be obtained, for example, by reacting 2,6-dimethyl-2,6-dialkylpiperidone of the formula

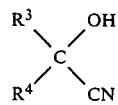

or a salt of such a piperidone with an equimolar amount or an α-hydroxamide of the formula $$\begin{array}{c} R^3 \diagdown \phantom{C} \diagup OH \\ C \\ R^4 \diagup \phantom{C} \diagdown CONH_2 \end{array}$$

or with an equimolar amount of a cyaninhydrin of the formula $$\begin{array}{c} R^3 \diagdown \phantom{C} \diagup OH \\ C \\ R^4 \diagup \phantom{C} \diagdown CN \end{array}$$

in an organic solvent at a temperature of 20° to 100° C. and in the presence of a dehydrating agent. The preparation is known from the literature.

Examples of suitable compounds of the formula VIII are 2,7,7,9,9-Pentamethyl-1-oxa-3-oxo-4,8-diaza-spiro[4,5]decane, 2-Ethyl-7,7,9,9-tetramethyl-1-oxa-3-oxo-4,8-diaza-spiro-[4,5]decane 2-Propyl-7,7,9,9-tetramethyl-1-oxa-3-oxo-4,8-diaza-spiro-[4,5]decane 2-Butyl-7,7,9,9-tetramethyl-1-oxa-3-oxo-4,8-diaza-spiro-[4,5]decane 2-iso-Butyl-7,7,9,9-tetramethyl-1-oxa-3-oxo-4,8-diaza-spiro-[4,5]decane
2-Pentyl-7,7,9,9-tetramethyl-1-oxa-3-oxo-4,8-diaza-spiro-[4,5]decane
2-iso-Pentyl-7,7,9,9-tetramethyl-1-oxa-3-oxo-4,8-diazo-spiro[4,5]decane
2-iso-Heptyl-7,7,9,9-tetramethyl-1-oxa-3-oxo-4,8-diaza-spiro[4,5]decane
2-Phenyl-7,7,9,9-tetramethyl-1-oxa-3-oxo-4,8-diaza-spiro[4,5]decane
2,2,7,7,9,9-Hexamethyl-1-oxa-3-oxo-4,8-diaza-spiro-4,5]decane
2,2,7,7,8,9,9-Heptamethyl-1-oxa-3-oxo-4,8-diaza-spiro-4,5]decane
2-2-Diethyl-7,7,9,9-tetramethyl-1-oxa-3-oxo-4,8-diaza-spiro[4,5]decane
2,2-Diethyl-7,7,8,9,9-pentamethyl-1-oxa-3-oxo-4,8-diaza-spiro[4,5]decane
2,2-Dipropyl-7,7,9,9-tetramethyl-1-oxa-3-oxo-4,8-diaza-spiro[4,5]decane
2,2-Dibutyl-7,7,9,9-tetramethyl-1-oxa-3-oxo-4,8-diaza-spiro[4,5]decane
2,2-Dipentyl-7,7,9,9-tetramethyl-1-oxa-3-oxo-4,8-diaza-spiro[4,5]decane
2-Ethyl-2,7,7,9,9-pentamethyl-1-oxa-3-oxo-4,8-diaza-spiro[4,5]decane
2-Propyl-2,7,7,9,9-pentamethyl-1-oxa-3-oxo-4,8-diaza-spiro[4,5]decane
2-iso-Propyl-2,7,7,9,9-pentamethyl-1-oxa-3-oxo-4,8-diaza-spiro[4,5]decane
2-Butyl-2,7,7,9,9-pentamethyl-1-oxa-3-oxo-4,8-diaza-spiro[4,5]decane
2-iso-Butyl-2,7,7,9,9-pentamethyl-1-oxa-3-oxo-4,8-diaza-spiro[4,5]decan
2-Pentyl-2,7,7,9,9-pentamethyl-1-oxa-3-oxo-4,8-diaza-spiro[4,5]decane
2-iso-Pentyl-2,7,7,9,9-pentamethyl-1-oxa-3-oxo-4,8-diaza-spiro[4,5]decane
2-Hexyl-2,7,7,9,9-pentamethyl-1-oxa-3-oxo-4,8-diaza-spiro[4,5]decane
2-Heptyl-2,7,7,9,9-pentamethyl-1-oxa-3-oxo-4,8-diaza-spiro[4,5]decane
2-Nonyl-2,7,7,9,9-pentamethyl-1-oxa-3-oxo-4,8-diaza-spiro[4,5]decane
2-Undecyl-2,7,7,9,9-pentamethyl-1-oxa-3-oxo-4,8-diaza-spiro[4,5]decane
2-Ethyl-2-butyl-7,7,9,9-tetramethyl-1-oxa-3-oxo-4,8-diaza-spiro[4,5]decane
2-Ethyl-2-pentyl-7,7,9,9-tetramethyl-1-oxa-3-oxo-4,8-diaza-spiro[4,5]decane
2-Ethyl-2-iso-pentyl-7,7,9,9-tetramethyl-1-oxa-3-oxo-4,8-diaza-spiro[4,5]decane
2,2,7,7,9,9-Hexamethyl-1-oxa-3-oxo-4,8-diaza-8-acetyl-spiro[4,5]decane
2,2-Diethyl-7,7,9,9-tetramethyl-1-oxa-3-oxo-4,8-diaza-8acetyl-spiro[4,5]decane
2,2,4,4-Tetramethyl-7-oxa-13-oxo-3,14-diaza-dispiro-5,1,4,2]tetradecane
2,2,4,4-Tetramethyl-7-oxa-14-oxo-3,15-diaza-dispiro-5,1,5,2]pentadecane and
2,2,4,4-Tetramethyl-7-oxa-20-oxo-3,21-diaza-dispiro-5,1,11,2]heneicosane.

Examples of suitable compounds of the formula IX are
Methyl acrylate,
Ethyl acrylate,
n-Butyl acrylate
iso-Butyl acrylate tert.-Butyl acrylate
2-Ethylhexyl acrylate
Octyl acrylate
Lauryl acrylate
Myristyl acrylate
2-Diethylaminoethyl acrylate
Methyl methacrylate
Ethyl methacrylate
n-Butyl methacrylate
iso-Butyl methacrylate
tert.-Butyl methacrylate
Lauryl methacrylate
Cyclohexyl methacrylate
Allyl methacrylate
2-Ethoxyethyl methacrylate
2-Dimethylaminoethyl methacrylate
Methyl crotonate
Ethyl crotonate
1,4-Butanediol diacrylate
1,6-Hexanediol diacrylate
2-Ethyl-2-hydroxymethyl-1,3-propanediol triacrylate
1,4-Butanediol dimethacrylate
Acrylamide
N,N'-Methylene-bis-(acrylamide)
N,N'-Ethylene-bis-(acrylamide)
N,N'-Hexamethylene-bis-(acrylamide)
Glyoxal-bis-(acrylamide)
2,2,6,6-Tetramethylpiperid-4-yl acrylate
2,2,6,6-Tetramethylpiperid-4-yl crotonate
2,2,6,6-Tetramethylpiperid-4-yl methacrylate
N-(2,2,6,6-Tetramethylpiperid-4-yl)-acrylamide
N-(2,2,6,6-Tetramethylpiperid-4-yl)-crotonamide
N-(2,2,6,6-Tetramethylpiperid-4-yl)-methacrylamide
N,N'-Bis-(2,2,6,6-tetramethylpiperid-4-yl)-N,N'-bis-(acrylamide)
N,N'-Bis-(2,2,6,6-tetramethylpiperid-4-yl)-N,N'-hexamethylene-bis-(acrylamide).

A further preparation method is the synthesis of the compounds of the formula I with X=—O— and n=1 and subsequent reaction with amines of the formula

$$R^7-[NHR^8]_n.$$

The solvent used for the process according to the invention is an aromatic hydrocarbon which is liquid at room temperature, preferably toluene or xylene.

The phase transfer catalyst added is preferably a polyethylene glycol dialkyl ether, a substituted phosphonium salt, for example a tetraalkylphosphonium halide, or a substituted ammonium salt, for example a tetraalkylammonium halide or trialkylbenzylammonium halide. In particular, triethylbenzylammonium chloride or a tetraalkylphosphonium bromide is added. The quantity is 0.05 to 20, preferably 0.1 to 10 and especially 1 to 10 mol%, relative to the compound of the formula VIII.

The compound IX is employed in a quantity of 1/n to 10/n, preferably 1/n to 3/n and especially 1/n to 1.5/n mol, relative to 1 mol of the compound VIII. n is as defined above.

The reaction temperature is 30° to 150°, preferably 50° to 120° and especially 70° to 120° C.

The reaction is carried out in the presence of a basic catalyst. An alkali metal, preferably sodium, which is used in a quantity of 1 to 30 mol%, preferably 2 to 10 mol%, relative to the compound of VIII, serves as a catalyst.

The process according to the invention has considerable advantages over the state of the art. Firstly, only a single solvent or solvent mixture, which is easy to handle industrially, is used. Surprisingly, the phase transfer catalyst has the effect that the reaction proceeds much faster and, above all, more completely, so that it is no longer necessary to employ a manifold excess of the compound IX; instead, a small excess suffices. Nevertheless, a higher yield is obtained and the quantity of by-products is reduced.

The compounds according to the invention, of the formula (I), are used above all as light stabilizers, for example for polyolefines, in particular polyethylene and polypropylene, ethylene/propylene copolymers, polybutylene, and also polystyrene, chlorinated polyethylene as well as polyvinyl chloride, polyester, polycarbonate, polymethyl methacrylates, polyphenylene oxides, polyamides, polyurethanes, polypropylene oxide, polyacetals, phenol-formaldehyde resins, epoxide resins, polyacrylonitrile and corresponding copolymers, and also ABS terpolymers. Preferably, the compounds prepared according to the invention are used for stabilizing polypropylene, low-molecular and high-molecular polyethylene, ethylene-propylene copolymers, polyvinyl chloride, polyester, polyamide, polyurethanes, polyacrylonitrile, ABS, terpolymers of acrylates, styrene and acrylonitrile, copolymers of styrene and acrylonitrile or styrene and butadiene, in particular for polypropylene, polyethylene, ethylene-propylene copolymer or ABS.

The compounds according to the invention can also be used for stabilizing natural materials, for example rubber, and also for lubricating oils. They are also suitable for stabilizing surface coatings.

The surface coatings can be of any types used in industrial surface-coating, preferably baking finishes.

The latter are baked at an elevated temperature, in order to obtain optimum properties. Wet surface coatings are preferred, which contain, as the binder: combinations of oil-modified polyester resins (oil alkyd resins) and melamine/formaldehyde resins or combinations of not self-crosslinking polyacrylate resins and melamine/formaldehyde resins or combinations of saturated polyesters and melamine/formaldehyde resins or self-crosslinking polyacrylate resins, or polyacrylate resins with copolymerized styrene. Two-component acrylate resin coatings, composed of acrylate resin containing hydroxyl groups and aliphatic or aromatic isocyanates, as well as thermoplastic polyacrylate resin coatings should also be mentioned. In addition, two-component polyurethane resin coatings, composed of polyester resins containing hydroxyl groups and/or polyether resins, hardened with aliphatic or aromatic isocyanates are also to be mentioned. For metalized coatings, thermoplastic polyacrylate resins or not self-crosslinking polyacrylate resins in combination with butanol-etherified melamine resins and also polyacrylate resins containing hydroxyl groups and hardened with aliphatic isocynates, are of particular importance. Powder coatings which are known per se and which have been treated, for example, with a solution of the compounds according to the invention, are also included.

The compounds according to the invention are incorporated in the materials, which are to be protected, by methods known per se, and it is also possible to provide monomers, prepolymers or precondensates with these stabilizers.

In addition to the compounds of the formula (I), further stabilizers can also be added to the plastics. Examples of such other compounds are antioxidants based on sterically hindered phenols, costabilizers containing sulfur or phosphorus, or a mixture of suitable sterically hindered phenols and sulfur- and/or phosphorus- containing compounds. Such compounds are, for example, benzofuran-2-one and/or indol in-2-one compounds, sterically hindered phenols such as stearyl β-(4-hydroxy-3,5-di-t-butylphenyl)propionate, methane tetrakis-[methylene 3-(3',5'-di-t-butyl4-hydroxyphenyl)-propionate], 1,3,3-tris-(2-methyl-4-hydroxy5-t-butylphenyl)-butane, 1,3,5-tris-(4-t-butyl-3-hydroxy 2,6-dimethylbenzyl)-1,3,5-triazine-2,4,6-(1H, 3H, 5H)trione, bis-(4-t-butyl-3-hydroxy-2,6-dimethylbenzyl) dithiolterephthalate, tris-(3,5-t-butyl-4-hydroxybenzyl) isocyanurate, the triester of β-(4-hydroxy-3,5-di-t-butylphenyl)-propionic acid with 1,3,5-tris-(2-hydroxyethyl)-striazine-2,4,6-(1H, 3H, 5H)-trione, glycol bis-[3,3-bis-(4'-hydroxy-3-t-butylphenyl)-butanoate], 2,3,5trimethyl2,4,6-tris-(3,5-di-t-butyl-4-hydroxybenzyl)-benzene, 2,2'methylene-bis-(4-methyl-6-t-butylphenyl) terephthalate, 4,4'-methylene-bis-(2,6-di-t-butylphenol), 4,4'-butylidene-bis-(t-butyl-meta-cresol), 4,4-thio-bis-(2-t-butyl5-methylphenol) and 2,2'-methylene-bis-(4-methyl-6-t-butylphenol). Co-stabilizers having an antioxidant action can also be added, such as, for example, sulfur-containing compounds, for example distearyl thiodipropionate, dilauryl thiodipropionate, methane-tetrakis-(methylene 3-hexyl-thiopropionate), methane-tetrakis-(methylene 3-dodecyl-thiopropionate) and dioctadecyl disulfide, or phosphorus-containing compounds such as, for example, trinonylphenyl phosphite, 4,9-distearyl-3,5,8,10-tetraoxadiphosphaspiro-undecane, tris-(2,4-t-butylphenyl) phosphite or tetrakis(2,4-di-t-butylphenyl) 4,4'-biphenylenediphosphonite.

The compounds of the formula I and their abovementioned mixtures can also be used in the presence of further additives. Such additives are known per se and belong, for example, to the group of aminoacrylic compounds, UV-absorbers and light stabilizers, such as 2-(2'-hydroxyphenyl)benzotriazoles, 2-hydroxybenzophenones, 1,3-bis-(2'-hydroxybenzoyl)-benzenes, salicylates, cinnamates, esters of substituted or unsubstituted benzoic acids, sterically hindered amines and oxalic acid diamides.

The application quantity of the compounds of the formula I, prepared according to the invention, is 0.01–5% by weight in the case of plastics, 20 to 80% by weight in the case of stabilizer concentrates and 0.02–5% by weight in the case of surface coatings.

EXAMPLE 1

24.0 g (0.1 mol) of 2,2,7,7,9,9-hexamethyl-1-oxa-3-oxo4,8-diazaspiro[4,5]decane (edukt I), 0.8 g of triethylbenzylammonium chloride and 0.2 g of sodium were added to 100 g of dried toluene, and the mixture was heated to 80° C. In the course of 30 minutes, 12.9 g [0.15 mol] of methyl acrylate were added dropwise. Stirring was continued for 6 hours at 80° C., the batch was then extracted by shaking with three times 50 ml of water, the organic phase was dried over Na$_2$SO$_4$ and filtered, and the toluene was distilled off. 31.6 g of a white solid (98% of theory) having a melting point of 75° C. remained. According to gas chromatography (GC), this product contained 0.2% by weight of 2,2,7,7,9,9-hexamethyl-1-oxa-3-oxo-4,8-diaza-spiro[4,5]decane, but no methyl acrylate.

EXAMPLE 2

The procedure as in Example 1 was followed, but 38.3 g (0.15 mol) of lauryl acrylate (technical mixture of about 53–55% of $C_{12}$-ester and about 42–45% of $C_{14}$-ester) were employed in place of methyl acrylate. This gave 52 g of an oily substance which, according to GC, still contained 0.06% by weight of edukt I.

EXAMPLE 3

As described in Example 1, 24.0 g (0.1 mol) of edukt I were reacted with 10.4 g [0.035 mol] of trimethylolpropane triacrylate. This gave 27.9 g of solid having a melting point of 80°–90° C.

EXAMPLE 4

32.6 g (0.1 mol) of the compound prepared according to Example 1 were dissolved in 100 g of xylene and dried under a water separator, and 5.8 g (0.05 mol) of hexamethylenediamine and 0.1 g of sodium hydride were added. In the course of 20 hours, about 3.2 g (0.1 mol) of methanol were distilled off via a column. After cooling, the precipitate was filtered off with suction and washed with boiling heptane. The colorless product had a melting point of 204° C.

EXAMPLE 5

8.6 g (0.036 mol) of 2,2,7,7,9,9-hexamethyl-1-oxa-3-oxo-4,8-diaza-spiro[4,5]decane were introduced into 100.0 g of toluene and dried by boiling under a water separator. 0.4 g of triethylbenzylammonium chloride, 0.2 g of sodium and 4.0 g (0.018 mol) of N,N'-hexamethylene-bis-(acrylamide) were then added at 80° C., and the mixture was stirred for about 12 hours at this temperature. The resulting precipitate was filtered off with suction and recrystallized from toluene. This gave 10.5 g of colorless product: melting point=204° C.; molecular mass measured 710, calculated 704.

CHN analysis: measured : C 64.7% H 9.8% N 11.1%. calculated : C 64.8% H 9.7% N 11.9%.

I claim:

1. A 1-oxa-3-oxo-4,8-diaza-sprio[4,5]decane compound of the formula I $$\left[ \begin{array}{c} R^2H_2C \quad CH_3 \qquad R^3 \\ \diagup \diagdown \qquad \qquad O \text{—} \phantom{R^4} R^4 \\ R^1\text{—}N \qquad \qquad \phantom{xxx} \\ \diagdown \diagup \qquad \qquad N\text{—}C\text{=}O \quad O \\ R^2H_2C \quad CH_3 \qquad \underset{R^5}{\overset{}{CH}}\text{—}\underset{R^6}{\overset{}{CH}}\text{—}\overset{\|}{C}\text{—}X\text{—}R^7 \end{array} \right]_n \quad (I)$$

wherein n is an integer from 1 to 4, $R^1$ is hydrogen, $C_1$–$C_4$-alkyl, benzyl, allyl, $C_2$–$C_{30}$-alkanoyl $C_3$–$C_{20}$-alkenoyl, $C_7$–$C_{11}$-aroyl, $C_8$–$C_{14}$-arylalkanoyl or $C_8$–$C_{20}$-alkylaryl, $R^2$ is hydrogen or $C_1$–$C_4$-alkyl, $R^3$ is hydrogen, $C_1$–$C_{18}$-alkyl, $C_5$–$C_{12}$-cycloalkyl, a phenyl or naphthyl group which can be substituted by chlorine or $C_1$–$C_4$-alkyl, or a $C_7$–$C_{12}$-phenylalkylene group which may be unsubstituted or substituted by $C_1$–$C_4$-alkyl, $R^4$ is hydrogen, $C_1$–$C_4$-alkyl, $C_5$–$C_{12}$-cycloalkyl, $C_1$–$C_3$-alkenyl which is substitute by —COOH, carbo-$C_1$–$C_4$-alkoxy or carbamoyl, a phenyl, naphthyl or pyridyl group which can be substituted by $C_1$–$C_4$-alkoxy or $C_1$–$C_4$-alkyl, or a $C_7$–$C_{12}$-phenylalkyl group which can be substituted by $C_1$–$C_4$-alkyl, or $R^3$ and $R^4$, together with the carbon atom linking them, form a $C_5$–$C_{12}$-cyloalkyl group, which can be monosubstituted to tetrasubstituted by $C_1$–$C_4$-alkyl groups, or a radical of the formula II $$\begin{array}{c} H_3C \quad CH_2R^2 \\ \diagup \diagdown \\ \diagdown \diagup N\text{—}R^1 \\ H_3C \quad CH_2R^2 \end{array} \quad (II)$$

wherein $R^1$ and $R^2$ are as defined above, $R^5$ is hydrogen, methyl, phenyl or carbo-$C_1$–$C_{21}$-alkoxy, $R^6$ is hydrogen or methyl, $R^7$ is, if n=1, hydrogen, $C_1$–$C_{21}$-alkyl, $C_2$–$C_{22}$-alkenyl, $C_7$–$C_{18}$-phenylalkyl, $C_5$–$C_{12}$-cycloalkyl, phenyl, naphyl, $C_7$–$C_{18}$-alkylphenyl, a radical of the formula $$\begin{array}{c} H_3C \quad CH_2R^2 \\ \diagup \diagdown \\ \diagdown \diagup N\text{—}R^1 \\ H_3C \quad CH_2R^2 \end{array}$$

in which $R^1$ and $R^2$ are as defined above, or $C_2$–$C_{20}$-alkyl which can be interrupted by —O— or $$\begin{array}{c} \text{—N—} \\ | \\ R^8 \end{array}$$

and/or substituted by a radical of the formula III $$\begin{array}{c} R^2H_2C \quad CH_3 \qquad R^3 \\ \diagup \diagdown \qquad \qquad O\text{—}\phantom{R^4}R^4 \\ R^1\text{—}N \qquad \qquad \phantom{xxx} \\ \diagdown \diagup \qquad \qquad N\text{—}C\text{=}O \quad O \\ R^2H_2C \quad CH_3 \quad \underset{R^5}{\overset{}{CH}}\text{—}\underset{R^6}{\overset{}{CH}}\text{—}\overset{\|}{C}\text{—}X\text{—} \end{array} \quad (III)$$

or by $C_1$–$C_{21}$-alkylcarboxyl, $R_1$, $R^2$, $R^3$, $R^4$, $R^5$, $R^6$ and X being as defined above and $R^8$ being hydrogne, $C_1$–$C_{10}$-alkyl or a radical $$\begin{array}{c} H_3C \quad CH_2R^2 \\ \diagup \diagdown \\ \diagdown \diagup N\text{—}R^1 \\ H_3C \quad CH_2R^2 \end{array}$$

in which $R^1$ and $R^2$ are as defined above, or $R^7$ is, if n=2, a straight-chain or branch $C_1$-$C_{30}$-alkylene, $C_2$-$C_{30}$-alkylene or phenyldialkylene, which radicals can be interrupted by —O— or

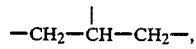

$R^8$ being as defined above, or $R^7$ is, if n=3 or 4, a radical of the formulae IV, V, VI or VII

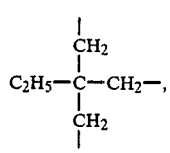   (IV)(V)

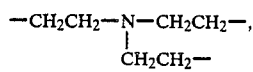   (VI)

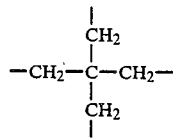   (VII)

and
X is —O— or

being as defined above.

2. A compound as claimed in claim 1, wherein
n is 1 or 2,
$R^1$ is hydrogen or acetyl,
$R^2$ is hydrogen,
$R^3$ and $R^4$ independently of one another are $C_1$-$C_7$-alkyl
$R^5$ and $R^6$ independently of one another are hydrogen or methyl,
$R^7$ is $C_2$-$C_{20}$-alkyl or $C_1$-$C_{30}$-alkylene, it being possible for these radicals to be interrupted by —O— or

$R^8$ being hydrogen, $C_1$-$C_{10}$-alkyl or

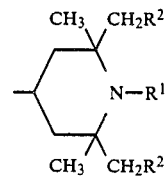

and
X is —O— or

$R^8$ being as defined above.

* * * * *